(12) United States Patent
Bearss et al.

(10) Patent No.: US 7,998,966 B2
(45) Date of Patent: Aug. 16, 2011

(54) AXL KINASE INHIBITORS

(75) Inventors: David J. Bearss, Cedar Hills, UT (US); Hariprasad Vankayalapati, Draper, UT (US); Yong Xu, Midvale, UT (US)

(73) Assignee: Supergen, Inc., Dublin, CA (US)

( * ) Notice: Subject to any disclaimer, the term of this patent is extended or adjusted under 35 U.S.C. 154(b) by 570 days.

(21) Appl. No.: 12/101,591

(22) Filed: Apr. 11, 2008

(65) Prior Publication Data

US 2008/0293733 A1    Nov. 27, 2008

Related U.S. Application Data

(60) Provisional application No. 60/911,832, filed on Apr. 13, 2007.

(51) Int. Cl.
*C07D 487/04* (2006.01)
*A61K 31/519* (2006.01)
*A61K 31/497* (2006.01)
*A61P 35/00* (2006.01)
*A61P 9/00* (2006.01)

(52) U.S. Cl. ............... 514/265.1; 544/280; 514/252.16
(58) Field of Classification Search .................. None
See application file for complete search history.

(56) References Cited

U.S. PATENT DOCUMENTS

| 6,169,088 B1 | 1/2001 | Matsuno et al. |
| 2005/0227992 A1 | 10/2005 | Hurley et al. |

FOREIGN PATENT DOCUMENTS

| WO | 02/16351 A1 | 2/2002 |
| WO | 2005/037825 A2 | 4/2005 |
| WO | 2006/054652 A1 | 5/2006 |
| WO | 2006/116733 A2 | 11/2006 |
| WO | 2007/020888 A1 | 2/2007 |
| WO | 2004/058772 A1 | 7/2007 |
| WO | 2008/055233 A1 | 5/2008 |

OTHER PUBLICATIONS

Matsuno et al., "Potent and Selective Inhibitors of Platelet-Derived Growth Factor Receptor Phosphorylation. 1. Synthesis, Structure—Activity Relationship, and Biological Effects of a New Class of Quinazoline Derivatives," Journal of Medicinal Chemistry 45(14): 3057-3066, Jul. 4, 2002.

Robertson et al., "A Comparison of the Requirements for Antitumour Activity and Antibacteriophage Lambda Activity for a Series of Non-intercalative DNA-binding Agents," European Journal of Cancer and Clinical Oncology 18(3): 271-279, Mar. 1, 1982.

Singh et al., "Chemotherapy of Filariasis—On the Search of New Agents Effective on the Reproductive System of Female Adult Worms," Zeitschrift Fuer Naturforschung, Section C, Biosciences 45(11/12): 1210-1214, Jan. 1, 1990.

Warner et al., "Identification of a lead small-molecule inhibitor of the Aurora kinases using a structure-assisted, fragment-based approach," Molecular Cancer Therapeutics 5(7): 1764-1773, Jul. 1, 2006.

*Primary Examiner* — Susanna Moore
(74) *Attorney, Agent, or Firm* — Seed IP Law Group PLLC

(57) ABSTRACT

Axl kinase inhibitory compounds are disclosed, as well as compositions and methods of using the same in the treatment of cancer and other conditions mediated by and/or associated with Axl kinase.

8 Claims, No Drawings

AXL KINASE INHIBITORS

CROSS-REFERENCE TO RELATED APPLICATION

This application claims the benefit under 35 U.S.C. §119 (e) of U.S. Provisional Patent Application No. 60/911,832, filed Apr. 13, 2007, where this provisional application is incorporated herein by reference in its entirety.

BACKGROUND

1. Technical Field

The present invention relates, in general, to compounds that inhibit protein kinase activity, and to compositions and methods related thereto.

2. Description of the Related Art

Cancer (and other hyperproliferative diseases) is characterized by uncontrolled cell proliferation. This loss of the normal control of cell proliferation often appears to occur as the result of genetic damage to cell pathways that control progress through the cell cycle. The cell cycle consists of DNA synthesis (S phase), cell division or mitosis (M phase), and non-synthetic periods referred to as gap 1 (G1) and gap 2 (G2). The M-phase is composed of mitosis and cytokinesis (separation into two cells). All steps in the cell cycle are controlled by an orderly cascade of protein phosphorylation and several families of protein kinases are involved in carrying out these phosphorylation steps. In addition, the activity of many protein kinases increases in human tumors compared to normal tissue and this increased activity can be due to many factors, including increased levels of a kinase or changes in expression of co-activators or inhibitory proteins.

Cells have proteins that govern the transition from one phase of the cell cycle to another. For example, the cyclins are a family of proteins whose concentrations increase and decrease throughout the cell cycle. The cyclins turn on, at the appropriate time, different cyclin-dependent protein kinases (CDKs) that phosphorylate substrates essential for progression through the cell cycle. Activity of specific CDKs at specific times is essential for both initiation and coordinated progress through the cell cycle. For example, CDK1 is the most prominent cell cycle regulator that orchestrates M-phase activities. However, a number of other mitotic protein kinases that participate in M-phase have been identified, which include members of the polo, aurora, and NIMA (Never-In-Mitosis-A) families and kinases implicated in mitotic checkpoints, mitotic exit, and cytokinesis.

Axl is a receptor tyrosine kinase (ligand: Growth Arrest Specific protein 6, Gas6) which is unique in having two tandem immunoglobulin-like repeats and two fibronectin type III repeats, a feature common in cellular adhesion molecules. For this reason, it has a family of its own, the Axl/Ufo subfamily of tyrosine kinases. The expression of Axl/Gas6 has been shown in a number of human malignancies, including ovarian, melanoma, renal cell carcinoma, uterine leiomyoma, uterine endometrial cancer, thyroid carcinoma, gastric cancer, breast cancer, NSCLC, CML, AML, colorectal carcinoma, prostate cancer, various lymphomas, and esophageal cancer. The Axl protooncogene is thus an attractive and valuable target for the discovery and development of new therapeutic agents.

Based on the involvement in a number of human malignancies, there is a need for the design of specific and selective inhibitors for the treatment of cancer and other conditions mediated and/or associated with Axl kinase. The present invention fulfills these needs and offers other related advantages.

BRIEF SUMMARY

The present invention is generally directed to compounds having the following general structure (I):

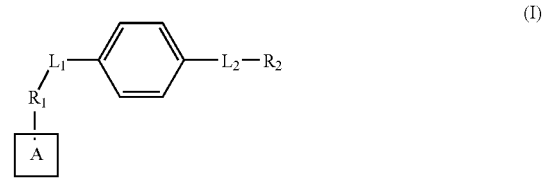

including stereoisomers, prodrugs and pharmaceutically acceptable salts thereof, where $L_1$, $R_1$, $L_2$, $R_2$ and ring moiety A are as defined herein.

These compounds have utility over a broad range of therapeutic applications, and may be used to treat diseases, such as cancer, that are mediated and/or associated (at least in part) with Axl kinase. Accordingly, in one aspect of the invention, the compounds described herein are formulated as pharmaceutically acceptable compositions for administration to a subject in need thereof.

In another aspect, the invention provides methods for treating or preventing a Axl kinase-mediated disease, such as cancer, which method comprises administering to a patient in need of such a treatment a therapeutically effective amount of a compound described herein or a pharmaceutically acceptable composition comprising said compound.

Another aspect relates to inhibiting Axl kinase activity in a biological sample, which method comprises contacting the biological sample with a compound described herein, or a pharmaceutically acceptable composition comprising said compound.

Another aspect relates to a method of inhibiting Axl kinase activity in a patient, which method comprises administering to the patient a compound described herein or a pharmaceutically acceptable composition comprising said compound.

These and other aspects of the invention will be apparent upon reference to the following detailed description. To that end, certain patent and other documents are cited herein to more specifically set forth various aspects of this invention. Each of these documents is hereby incorporated by reference in its entirety.

DETAILED DESCRIPTION

The present invention is generally directed to compounds having the following general structure according to Formula (I):

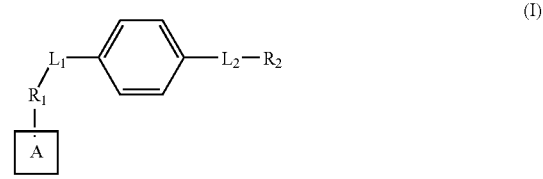

including stereoisomers, prodrugs and pharmaceutically acceptable salts thereof, where:

ring moiety A is selected from:

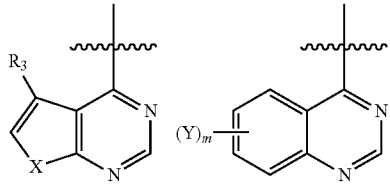

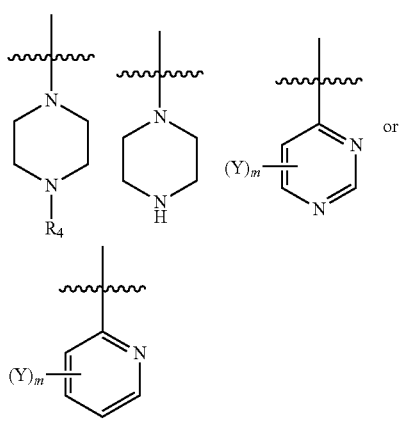

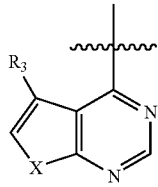

where:

$L_1$ is —NH—, —C(=S)NH—, —C(=S)NHS(=O)$_2$—, or —C(=O)NH—;

$R_1$ is optional and if present is piperazinyl;

$L_2$=—S(=O)$_2$NH—, —S(=O)$_2$— or —NH—;

$R_2$ is heterocycle, substituted heterocycle, or —C(=O)R where R is alkyl;

X is O, S or NH;

Y at each occurrence is independently halo, haloalkyl or alkoxy;

m is 0, 1, 2 or 3;

$R_3$ is —H, halo, haloalkyl, haloalkoxy, aryl or substituted aryl; and $R_4$ is —H, alkyl, substituted alkyl, aryl or substituted aryl, heteroaryl or substituted heteroaryl.

In an aspect of the invention, $L_1$ is —NH— and the other variables are as defined above for Formula (I).

In an embodiment of this aspect, $L_1$ is —NH—, ring moiety A is

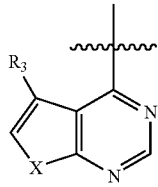

and the other variables are as defined above for Formula (I).

In another embodiment of this aspect, $L_1$ is —NH—, ring moiety A is

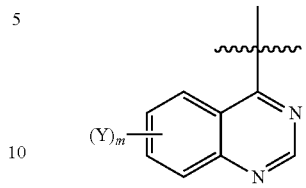

and the other variables are as defined above for Formula (I).

In another aspect of the invention, $L_1$ is —C(=S)NH— and the other variables are as defined above for Formula (I).

In an embodiment of this aspect of the invention, $L_1$ is —C(=S)NH—, ring moiety A is

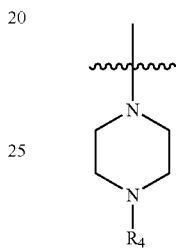

and the other variables are as defined above for Formula (I).

In another embodiment of this aspect of the invention, $L_1$ is —C(=S)NH—, ring moiety A is

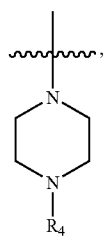

$R_4$ is heteroaryl or substituted heteroaryl, and the other variables are as defined above for Formula (I).

In another embodiment of this aspect of the invention, $L_1$ is —C(=S)NH—, ring moiety A is

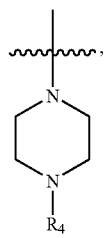

$R_4$ is —H or alkyl, and the other variables are as defined above for Formula (I).

In yet another aspect of the invention, $L_1$ is —C(=S)NHS (=O)$_2$— and the other variables are as defined above for Formula (I).

In an embodiment of this aspect, $L_1$ is —C(=S)NHS(=O)$_2$—, ring moiety A is

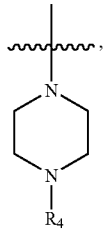

and the other variables are as defined above for Formula (I).

In still another aspect of the invention, $L_1$ is —C(=O)NH—, and the other variables are as defined above for Formula (I).

In an embodiment of this aspect, $L_1$ is —C(=O)NH—, ring moiety A is

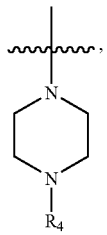

and the other variables are as defined above for Formula (I).

Unless otherwise stated the following terms used in the specification and claims have the meanings discussed below:

"Alkyl" refers to a saturated straight or branched hydrocarbon radical of one to six carbon atoms, preferably one to four carbon atoms, e.g., methyl, ethyl, propyl, 2-propyl, n-butyl, iso-butyl, tert-butyl, pentyl, hexyl, and the like, preferably methyl, ethyl, propyl, or 2-propyl. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, iso-pentyl, and the like. Representative saturated cyclic alkyls include cyclopropyl, cyclobutyl, cyclopentyl, cyclohexyl, —CH$_2$-cyclohexyl, and the like; while unsaturated cyclic alkyls include cyclopentenyl, cyclohexenyl, —CH$_2$-cyclohexenyl, and the like. Cyclic alkyls are also referred to herein as a "cycloalkyl." Unsaturated alkyls contain at least one double or triple bond between adjacent carbon atoms (referred to as an "alkenyl" or "alkynyl", respectively.) Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like, preferably methylene, ethylene, or propylene.

"Cycloalkyl" refers to a saturated cyclic hydrocarbon radical of three to eight carbon atoms, e.g., cyclopropyl, cyclobutyl, cyclopentyl or cyclohexyl.

"Alkoxy" means a radical —OR$_a$ where R$_a$ is an alkyl as defined above, e.g., methoxy, ethoxy, propoxy, butoxy and the like.

"Halo" means fluoro, chloro, bromo, or iodo, preferably fluoro and chloro.

"Haloalkyl" means alkyl substituted with one or more, preferably one, two or three, same or different halo atoms, e.g., —CH$_2$Cl, —CF$_3$, —CH$_2$CF$_3$, —CH$_2$CCl$_3$, and the like.

"Haloalkoxy" means a radical —OR$_b$ where R$_b$ is an haloalkyl as defined above, e.g., trifluoromethoxy, trichloroethoxy, 2,2-dichloropropoxy, and the like.

"Acyl" means a radical —C(O)R$_c$ where R$_c$ is hydrogen, alkyl, or haloalkyl as defined herein, e.g., formyl, acetyl, trifluoroacetyl, butanoyl, and the like.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthyl and anthracenyl. The aryl group may be substituted or unsubstituted. When substituted, the aryl group is substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, phenoxy, heteroaryl, heteroaryloxy, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be substituted or unsubstituted. When substituted, the heteroaryl group is substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Carbocycle" refers to a saturated, unsaturated or aromatic ring system having 3 to 14 ring carbon atoms. The term "carbocycle", whether saturated or partially unsaturated, also refers to rings that are optionally substituted. The term "carbocycle" includes aryl. The term "carbocycle" also includes aliphatic rings that are fused to one or more aromatic or nonaromatic rings, such as in a decahydronaphthyl or tetrahydronaphthyl, where the radical or point of attachment is on the aliphatic ring. The carbocycle group may be substituted or unsubstituted. When substituted, the carbocycle group is substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heterocycle" refers to a saturated, unsaturated or aromatic cyclic ring system having 3 to 14 ring atoms in which one, two or three ring atoms are heteroatoms selected from N, O, or S(O)$_m$ (where m is an integer from 0 to 2), the remaining ring atoms being C, where one or two C atoms may optionally be replaced by a carbonyl group. The term "heterocycle" includes heteroaryl. The heterocyclyl ring may be optionally substituted independently with one or more, preferably one, two, or three substituents selected from alkyl (wherein the alkyl may be optionally substituted with one or two substituents), haloalkyl, cycloalkylamino, cycloalkylalkyl, cycloalkylaminoalkyl, cycloalkylalkylaminoalkyl, cyanoalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aralkyl, heteroaralkyl, aryl, heteroaryl, carbocycle, heterocycle (wherein the aryl, heteroaryl, carbocycle or heterocycle may be optionally substituted), aralkyl, heteroaralkyl, saturated or unsaturated heterocycloamino, saturated or unsaturated heterocycloaminoalkyl, and —COR$_d$ (where R$_d$ is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, 4-cyclopropylmethylpiperazino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. In certain embodiments, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Optional" or "optionally" means that the subsequently described event or circumstance may but need not occur, and that the description includes instances where the event or circumstance occurs and instances in which it does not. For example, "heterocyclic group optionally substituted with an alkyl group" means that the alkyl may but need not be present, and the description includes situations where the heterocycle group is substituted with an alkyl group and situations where the heterocycle group is not substituted with the alkyl group.

Lastly, the term "substituted" as used herein means any of the above groups (e.g., alkyl, aryl, heteroaryl, carbocycle, heterocycle, etc.) wherein at least one hydrogen atom is replaced with a substituent. In the case of an oxo substituent ("=O") two hydrogen atoms are replaced. "Substituents" within the context of this invention include halogen, hydroxy, oxo, cyano, nitro, amino, alkylamino, dialkylamino, alkyl, alkoxy, thioalkyl, haloalkyl (e.g., —CF$_3$), hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_e$R$_f$, —NR$_e$C(=O)R$_f$, NR$_e$C(=O)NR$_e$R$_f$, NR$_e$C(=O)OR$_f$, —NR$_e$SO$_2$R$_f$, —OR$_e$, C(=O)R$_e$, —C(=O)OR$_e$, —C(=O)NR$_e$R$_f$, —OC(=O)NR$_e$R$_f$, —SH, —SR$_e$, —SOR$_e$, —S(=O)$_2$R$_e$, —OS(=O)$_2$R$_e$, —S(=O)$_2$OR$_e$, wherein R$_e$ and R$_f$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

In a more specific aspect of structure (I) above, L$_1$ is —C(=S)NH—, —C(=S)NHS(=O)$_2$—, or —C(=O)NH—, and R$_1$ is piperazinyl.

In a more specific aspect of structure (I), R$_1$ is piperazinyl, ring moiety A is:

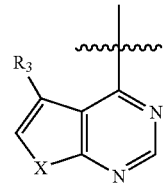

and the compounds have the following structure (II):

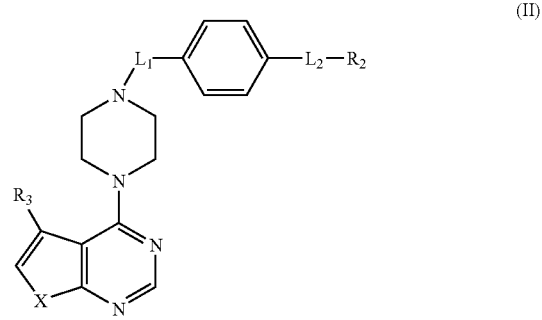

(II)

In a more specific aspect of structures (I) and (II) above, L$_2$=—S(=O)$_2$NH—.

In a more specific aspect of structures (I) and (II), R$_2$ is heteroaryl, substituted heteroaryl, or —C(=O)R where R is alkyl;

In a more specific aspect of structures (I) and (II), R$_2$ is —C(=O)R where R is alkyl, or R$_2$ is selected from:

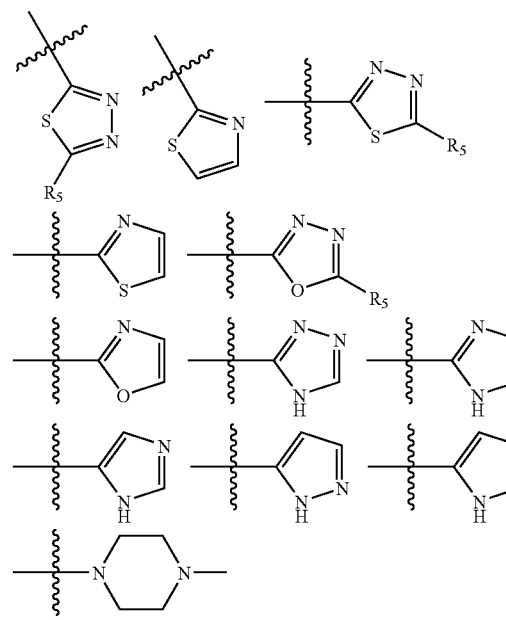

where R$_5$ is —H or alkyl, e.g., C$_1$-C$_4$ alkyl.

In a more specific aspect of structures (I) and (II), R$_3$ is —H, halo, haloalkyl, haloalkoxy, phenyl or substituted phenyl.

In a more specific aspect of structures (I) and (II) above, $R_3$ is:

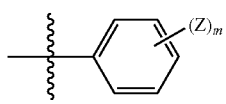

where each occurrence of Z is independently H, alkoxy, halo or haloalkyl haloalkoxy, —$NO_2$, —$NH_2$—CN, —S(=O)$_2$CH$_3$ and where m is 0, 1, 2 or 3.

In a more specific aspect of structures (I) above, $L_1$ is —NH— and $R_1$ absent.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog (Cahn, R., Ingold, C., and Prelog, V. Angew. Chem. 78:413-47, 1966; Angew. Chem. Internat. Ed. Eng. 5:385-415, 511, 1966), or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Ch. 4 of ADVANCED ORGANIC CHEMISTRY, 4th edition, March, J., John Wiley and Sons, New York City, 1992).

The compounds of the present invention may exhibit the phenomena of tautomerism and structural isomerism. This invention encompasses any tautomeric or structural isomeric form and mixtures thereof which possess the ability to modulate Axl kinase activity and is not limited to, any one tautomeric or structural isomeric form.

It is contemplated that a compound of the present invention would be metabolized by enzymes in the body of the organism such as human being to generate a metabolite that can modulate the activity of the protein kinases. Such metabolites are within the scope of the present invention.

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found, for example, in REMINGTON'S PHARMACOLOGICAL SCIENCES, Mack Publishing Co., Easton, Pa., latest edition.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts may include: (1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D)- or (L)-malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of the present invention may also act, or be designed to act, as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), phosphate, amide, carbamate or urea.

"Therapeutically effective amount" refers to that amount of the compound being administered which will relieve to some extent one or more of the symptoms of the disorder being treated. In reference to the treatment of cancer, a therapeutically effective amount refers to that amount which has the effect of: (1) reducing the size of the tumor; (2) inhibiting tumor metastasis; (3) inhibiting tumor growth; and/or (4) relieving one or more symptoms associated with the cancer.

The term "protein kinase-mediated condition" or "disease", as used herein, means any disease or other deleterious condition in which a protein kinase is known to play a role. The term "protein kinase-mediated condition" or "disease" also means those diseases or conditions that are alleviated by treatment with a protein kinase inhibitor. Such conditions include, without limitation, cancer and other hyperproliferative disorders. In certain embodiments, the cancer is a cancer of colon, breast, stomach, prostate, pancreas, or ovarian tissue.

The term "Axl kinase-mediated condition" or "disease", as used herein, means any disease or other deleterious condition in which Axl kinase is overexpressed, overactive and/or is known to play a role. The term "Axl kinase-mediated condition" also means those diseases or conditions that are alleviated by treatment with an Axl kinase inhibitor.

As used herein, "administer" or "administration" refers to the delivery of an inventive compound or of a pharmaceutically acceptable salt thereof or of a pharmaceutical composition containing an inventive compound or a pharmaceutically acceptable salt thereof of this invention to an organism for the purpose of prevention or treatment of a protein kinase-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. In certain embodiments, the preferred routes of administration are oral and intravenous.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. In this way, the liposomes may be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in any conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also. Pharmaceutical compositions which may also be used include hard gelatin capsules. The capsules or pills may be packaged into brown glass or plastic bottles to protect the active compound from light. The containers containing the active compound capsule formulation are preferably stored at controlled room temperature (15-30° C.).

For administration by inhalation, the compounds for use according to the present invention may be conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD:D5W) consists of VPD diluted 1:1 with a 5% dextrose in water solution. This cosolvent system dissolves hydrophobic compounds well, and itself produces low toxicity upon systemic administration. Naturally, the proportions of such a cosolvent system may be varied considerably without destroying its solubility and toxicity characteristics. Furthermore, the identity of the cosolvent components may be varied: for example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the protein kinase-modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g., sodium hydroxide (NaOH), potassium hydroxide (KOH), calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of protein kinase activity and/or the treatment or prevention of a protein kinase-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the protein kinase activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, 9th ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 mg/m$^2$ to 1500 mg/m$^2$ per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

As mentioned above, the compounds and compositions of the invention will find utility in a broad range of diseases and conditions mediated by protein kinases, including diseases and conditions mediated by Axl kinase. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

The inventive compound can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-II inhibitors include Vioxx, CELEBREX (celecoxib), valdecoxib, paracoxib, rofecoxib, and Cox 189.

Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and compounds selected from: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

Other anti-angiogenesis agents, other COX-II inhibitors and other MMP inhibitors, can also be used in the present invention.

An inventive compound can also be used with other signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, such as HERCEPTIN (Genentech, Inc., South San Francisco, Calif.). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems, Inc., New York, N.Y.), the compounds ZD-1839 (AstraZeneca), BIBX-1382 (Boehringer Ingelheim), MDX-447 (Medarex Inc., Annandale, N.J.), and OLX-103 (Merck & Co., Whitehouse Station, N.J.), and EGF fusion toxin (Seragen Inc., Hopkinton, Mass.).

These and other EGFR-inhibiting agents can be used in the present invention. VEGF inhibitors, for example SU-5416 and SU-6668 (Sugen Inc., South San Francisco, Calif.), can also be combined with an inventive compound. VEGF inhibitors are described in, for example, WO 01/60814 A3 (published Aug. 23, 2001), WO 99/24440 (published May 20, 1999), PCT International Application PCT/IB99/00797 (filed May 3, 1999), WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc., Kirkland, Wash.); anti-VEGF monoclonal antibody of Genentech, Inc.; and angiozyme, a synthetic ribozyme from Ribozyme (Boulder, Colo.) and Chiron (Emeryville, Calif.). These and other VEGF inhibitors can be used in the present invention as described herein. pErbB2 receptor inhibitors, such as GW-282974 (Glaxo Wellcome plc), and the monoclonal antibodies AR-209 (Aronex Pharmaceuticals Inc., The Woodlands, Tex.) and 2B-1 (Chiron), can furthermore be combined with an inventive compound, for example, those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Pat. No. 6,284,764 (issued Sep. 4, 2001), incorporated in its entirety herein by reference. The erbB2 receptor inhibitor compounds and substance described in the aforementioned PCT applications, U.S. patents, and U.S. provisional applications, as well as other compounds and substances that inhibit the erbB2 receptor, can be used with an inventive compound, in accordance with the present invention.

An inventive compound can also be used with other agents useful in treating cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1.

The above method can also be carried out in combination with radiation therapy, wherein the amount of an inventive compound in combination with the radiation therapy is effective in treating the above diseases.

Techniques for administering radiation therapy are known in the art, and these techniques can be used in the combination therapy described herein. The administration of the compound of the invention in this combination therapy can be determined as described herein.

The invention will be further understood upon consideration of the following non-limiting Examples.

EXAMPLES
Identification of Axl Kinase Inhibitors
Representative EXAMPLES of the invention are set forth below in Tables 1, 2 and 3.
TABLE 1
Thienopyrimidine series as Axl kinase inhibitors
| EXAMPLE | Structure |
|---|---|
| 1 | 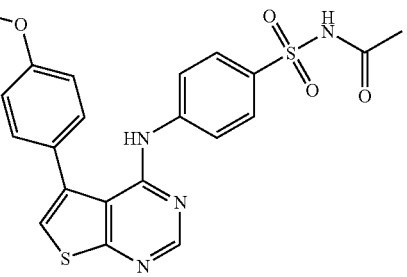 |
| 2 | 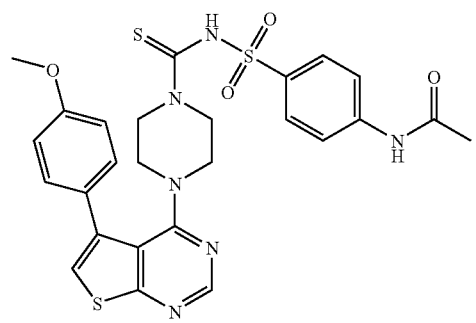 |
| 3 | 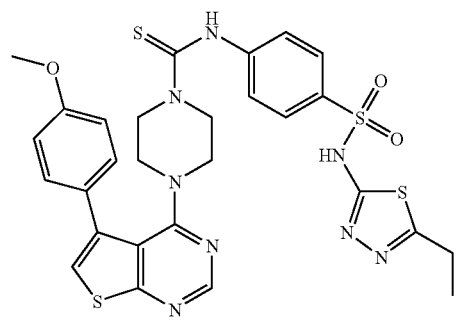 |
TABLE 2
Pyrrolopyrimidine series as Axl kinase inhibitors
| EXAMPLE | Structure |
|---|---|
| 4 | 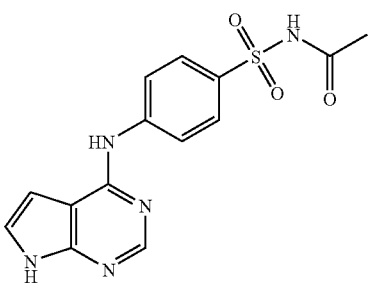 |
| 5 | 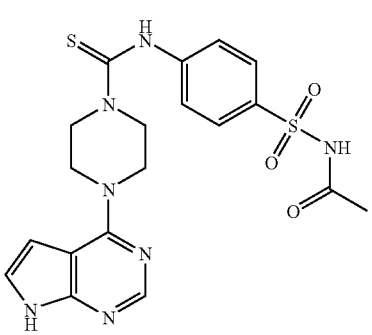 |
| 6 | 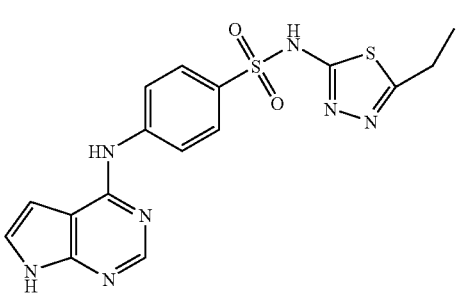 |
| 7 | 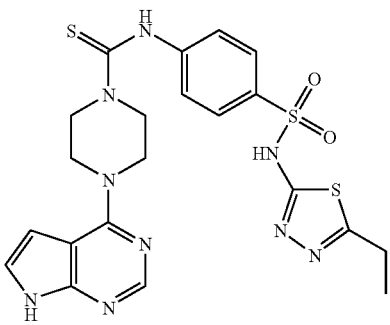 |

TABLE 2-continued
Pyrrolopyrimidine series as Axl kinase inhibitors
| EXAMPLE | Structure |
|---|---|
| 8 | 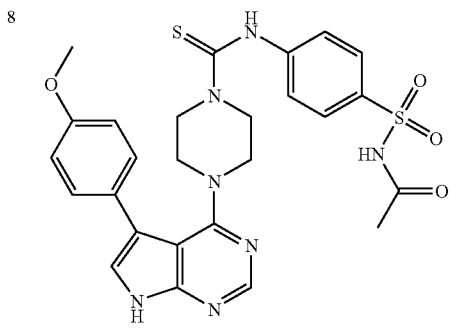 |
| 9 | 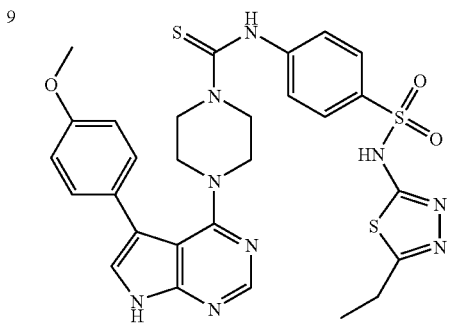 |
| 10 | 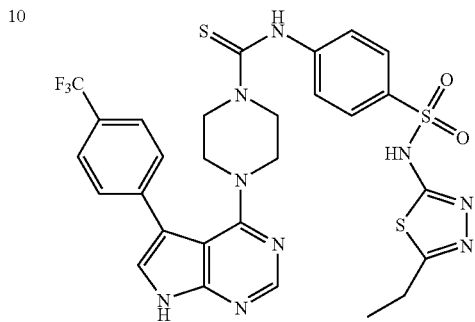 |
| 11 | 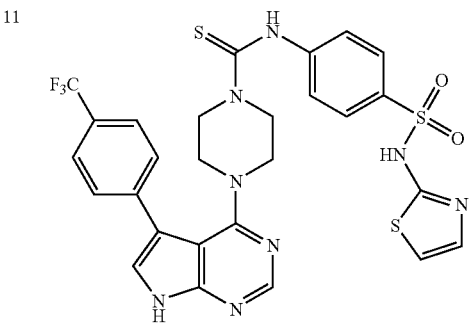 |
| 12 | 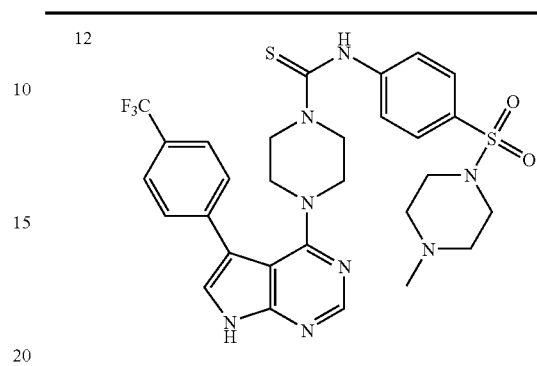 |
| 13 | 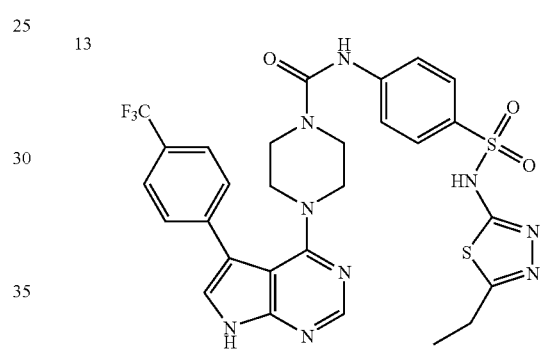 |
| 14 | 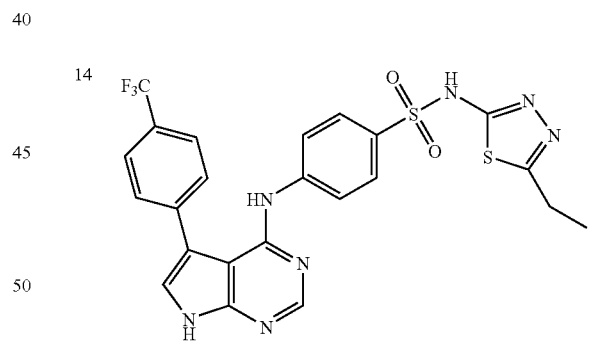 |
| 15 | 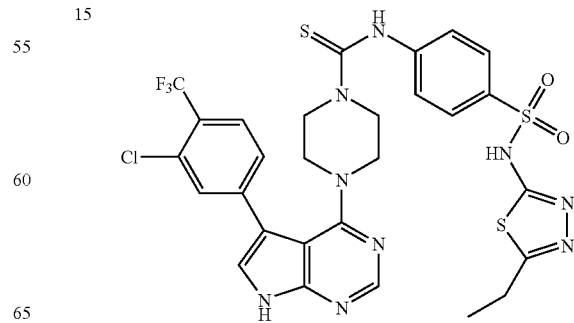 |

TABLE 2-continued
Pyrrolopyrimidine series as Axl kinase inhibitors
| EXAMPLE | Structure |
|---|---|
| 16 | 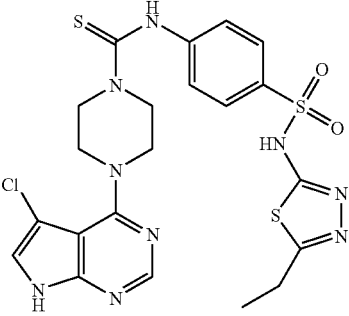 |
TABLE 3
Pyridine, Pyrimidine and Quinazoline series as Axl kinase inhibitors
| EXAMPLE | Structure |
|---|---|
| 17 | 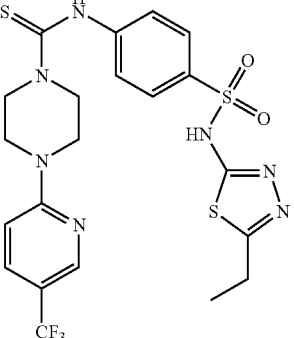 |
| 18 | 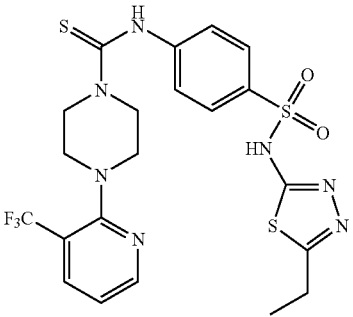 |
| 19 | 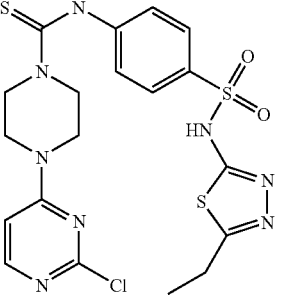 |
TABLE 3-continued
Pyridine, Pyrimidine and Quinazoline series as Axl kinase inhibitors
| EXAMPLE | Structure |
|---|---|
| 20 | 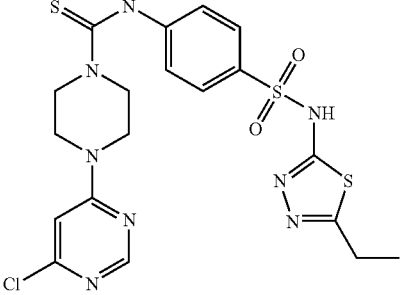 |
| 21 | 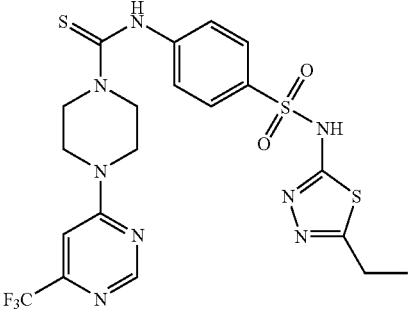 |
| 22 | 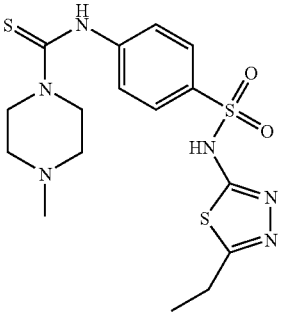 |
| 23 | 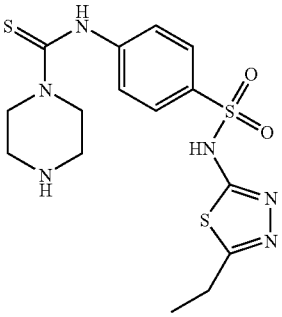 |

TABLE 3-continued

Pyridine, Pyrimidine and Quinazoline series as Axl kinase inhibitors

| EXAMPLE | Structure |
|---|---|
| 24 | 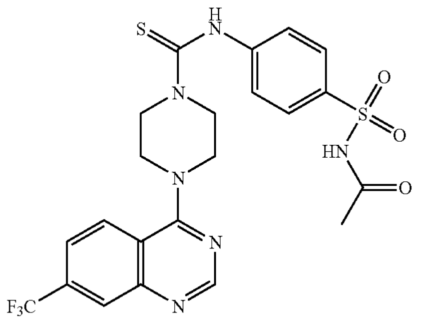 |
| 25 | 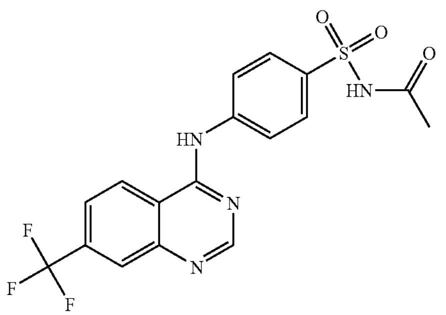 |
| 26 | 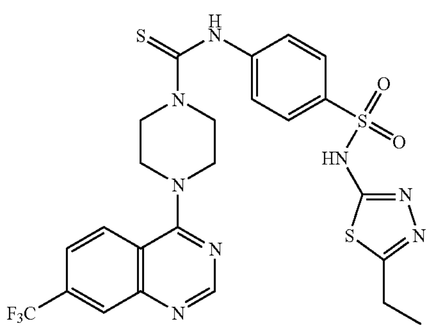 |

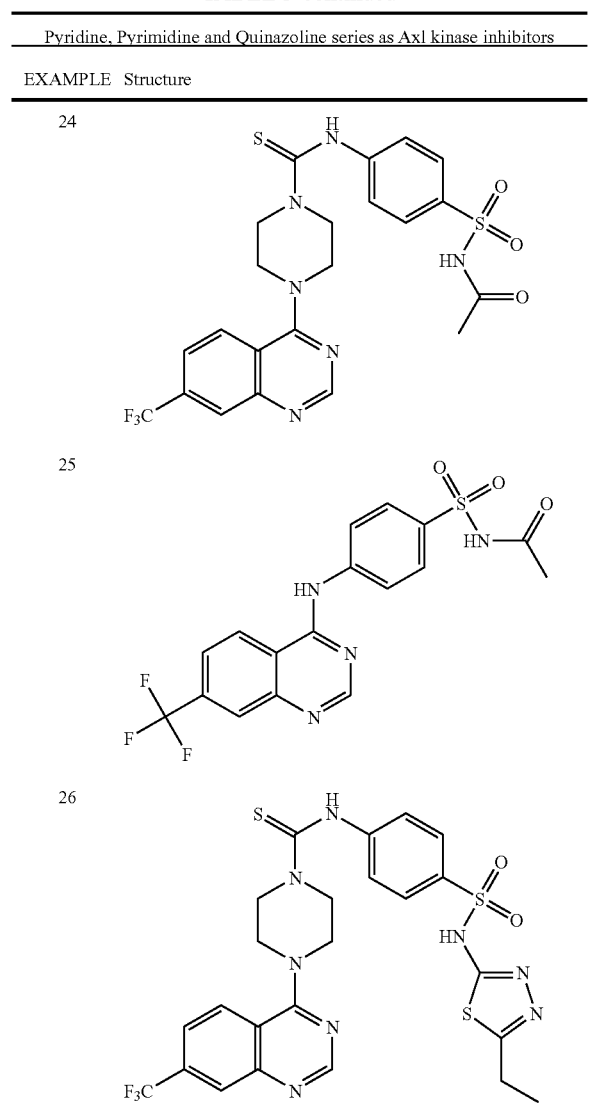

General Synthesis of Representative Compounds

Compounds of the invention may be made by one of ordinary skill in the chemical arts using conventional synthetic procedures, as well as by the general reaction schemes and examples described below.

Scheme 1
General Synthesis of 5-Aryl pyrrolo[2,3-d]pyrimidine Compounds

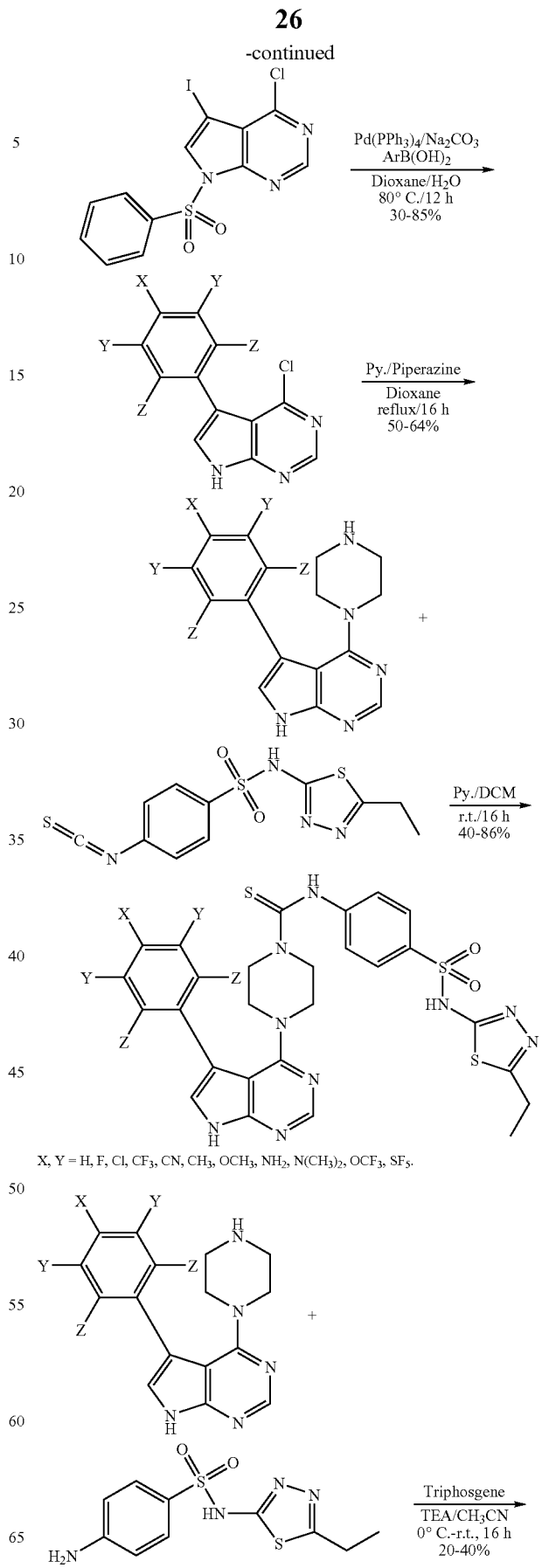

X, Y = H, F, Cl, CF$_3$, CN, CH$_3$, OCH$_3$, NH$_2$, N(CH$_3$)$_2$, OCF$_3$, SF$_5$.

-continued

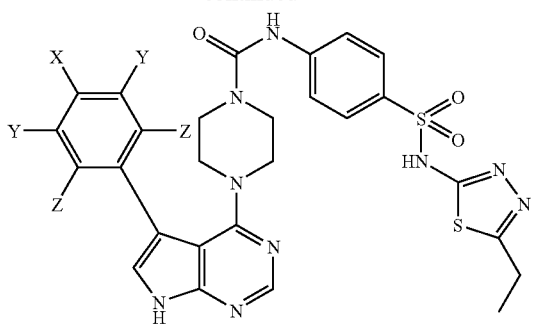

X, Y = H, F, Cl, CF$_3$, CN, CH$_3$, OCH$_3$, NH$_2$, N(CH$_3$)$_2$, OCF$_3$, SF$_5$.

Example 27

4-Chloro-5-iodo-7-benzenesulfonyl-7H-pyrrolo[2,3-d]pyrimidine $^1$H-NMR (CD$_3$OD/400 MHz): 8.75 (s, 1H), 8.22 (dm, J=6.5 Hz, 2H), 7.94 (s, 1H), 7.68 (tm, J=8.6 Hz, 1H), 7.55 (tm, J=8.6 Hz, 2H). MS (ES+, m/z): 419.9 (M$^+$+1, 100.0).

Example 28

7-Benzenesulfonyl-4-chloro-5-(4-methoxyphenyl)-7H-pyrrolo[2,3-d]pyrimidine $^1$H-NMR (CDCl$_3$/400 MHz): 8.76 (s, 1H), 8.23 (d, J=7.9 Hz, 2H), 7.70 (s, 1H), 7.65 (t, J=7.6 Hz, 1H), 7.55 (t, J=7.6 Hz, 3H), 7.37 (d, J=8.5 Hz, 2H), 6.95 (d, J=8.6 Hz, 2H), 3.84 (s, 3H). MS (ES+, m/z): 400.0 (M$^+$+1, 100.0), 402.0 (M$^+$+1, 45.0).

Example 29

4-Piperazine-5-(4-methoxylbenzene)-7H-pyrrolo[2,3-d]pyrimidine $^1$H-NMR (CD$_3$OD/CDCl$_3$/400 MHz): 8.27 (s, 1H), 7.38 (dd, J=6.5, 2.1 Hz, 2H), 7.12 (s, 1H), 6.95 (dd, J=6.5, 2.1 Hz, 2H), 3.82 (s, 3H), 3.29 (m, 4H), 2.63 (m, 4H). MS (ES+, m/z): 310.1 (M$^+$+1, 100.0).

Example 8

N-(4-(4-(5-(4-methoxyphenyl)-7H-pyrrolo[2,3-d]pyrimidin-4-yl)piperazine-1-carbothioamido)phenyl-sulfonyl)acetamide $^1$H-NMR (CD$_3$OD/400 MHz): 8.32 (s, 1H), 7.79 (d, J=8.9 Hz, 2H), 7.42 (d, J=8.9 Hz, 2H), 7.35 (d, J=8.9 Hz, 2H), 7.23 (s, 1H), 7.01 (d, J=8.9 Hz, 2H), 3.83 (s, 3H), 3.80 (m, 4H), 3.37 (m, 4H), 1.85 (s, 3H). MS (ES+, m/z): 566.1 (M$^+$+1, 100.0).

Example 9

N-(4-(N-(5-ethyl-1,3,4-thiadiazol-2-yl)sulfamoyl)phenyl)-4-(5-(4-methoxyphenyl)-(7H-pyrrolo[2,3-d]pyrimidin-4-yl)piperazine-1-carbothioamide $^1$H-NMR (CD$_3$OD/CDCl$_3$/400 MHz): 8.31 (s, 1H), 7.74 (d, J=8.9 Hz, 2H), 7.34 (d, J=8.9 Hz, 4H), 7.13 (s, 1H), 6.95 (d, J=8.9 Hz, 2H), 3.82 (s, 3H), 3.78 (m, 4H), 3.40 (m, 4H), 2.80 (q, J=7.5 Hz, 2H), 1.27 (t, J=7.5 Hz, 3H). MS (ES+, m/z): 636.1 (M$^+$+1, 100.0).

Example 30

4-Chloro-5-(4-methoxylbenzene)-7H-pyrrolo[2,3-d]pyrimidine $^1$H-NMR (CD$_3$OD/400 MHz): 8.51 (s, 1H), 7.47 (d, J=8.9 Hz, 2H), 7.37 (s, 1H), 6.92 (d, J=8.9 Hz, 2H), 3.82 (s, 3H). MS (ES+, m/z): 260.0 (M$^+$+1, 100.0).

Example 31

4-Chloro-5-(4-trifluoromethylphenyl)-7H-pyrrolo[2,3-d]pyrimidine $^1$H-NMR (CD$_3$OD/400 MHz): 8.58 (s, 1H), 7.72 (m, 4H). MS (ES+, m/z): 298.0 (M$^+$+1, 100.0).

Example 32

4-Piperazine-5-(4-trifluoromethylbenzene)-N-benzenesulfonyl-7H-pyrrolo[2,3-d]pyrimidine $^1$H-NMR (CD$_3$OD/400 MHz): 8.60 (s, 1H), 7.96 (m, 4H), 2.93 (m, 8H). MS (ES+, m/z): 348.1 (M$^+$+1, 100.0).

Example 10

N-(4-(N-(5-ethyl-1,3,4-thiadiazo-2-yl)sulfamoyl)phenyl)-5-(4-trifluoromethylphenyl)-7H-pyrrolo[2,3-d]pyrimidin-4-yl)piperazine-1-carbothioamide $^1$H-NMR (CD$_3$OD/CDCl$_3$/400 MHz): 8.14 (s, 1H), 7.51 (d, J=8.5 Hz, 2H), 7.44 (dd, J=7.5 Hz, 4H), 7.09 (d, J=8.5 Hz, 2H), 7.07 (s, 1H), 3.56 (t, J=4.4 Hz, 4H), 3.19 (t, J=4.4 Hz, 4H), 2.76 (q, J=7.5 Hz, 2H), 0.92 (t, J=7.5 Hz, 3H). MS (ES+, m/z): 674.1 (M$^+$+1, 100.0).

Example 11

N-(4-(N-thiazol-2-ylsulfamoyl)phenyl)-4-(5-(4-(trifluoromethyl)phenyl)-7H-pyrrolo[2,3-d]pyrimidin-4-yl)piperazine-1-carbothioamide $^1$H-NMR (CD$_3$OD/CDCl$_3$/400 MHz): 7.97 (s, 1H), 7.38 (d, J=6.8 Hz, 2H), 7.29 (d, J=1.7 Hz, 4H), 7.00 (d, J=6.8 Hz, 2H), 6.95 (m, 1H), 6.57 (d, J=4.6 Hz, 1H), 6.19 (d, J=4.6 Hz, 1H), 3.42 (t, J=4.4 Hz, 4H), 3.03 (t, J=4.4 Hz, 4H), 2.75 (q, J=7.5 Hz, 2H), 0.90 (t, J=7.5 Hz, 3H). MS (ES+, m/z): 645.1 (M+1, 100.0).

Example 12

N-(4-(4-methylpiperazin-1-ylsulfonyl)phenyl)-4-(5-(4-(trifluoromethyl)phenyl)-7H-pyrrolo[2,3-d]pyrimidin-4-yl)piperazine-1-carbothioamide $^1$H-NMR (CD$_3$OD/CDCl$_3$/400 MHz): 8.20 (s, 1H), 7.46 (m, 6H), 7.28 (d, J=8.5 Hz, 2H), 7.11 (s, 1H), 3.63 (t, J=4.4 Hz, 4H), 3.26 (t, J=4.4 Hz, 4H), 2.86 (t, J=4.5 Hz, 4H), 2.30 (t, J=4.5 Hz, 4H), 2.07 (s, 3H), 0.90 (t, J=7.5 Hz, 3H). MS (ES+, m/z): 645.2 (M$^+$+1, 30.0).

Example 13

N-(4-(N-(5-ethyl-1,3,4-thiadiazo-2-yl)sulfamoyl)phenyl)-5-(4-trifluoromethylphenyl)-7H-pyrrolo[2,3-d]pyrimidin-4-yl)piperazine-1-carboamide $^1$H-NMR (CD$_3$OD/CDCl$_3$/400 MHz): 8.35 (s, 1H), 7.73 (d, J=8.9 Hz, 2H), 7.69 (m, 4H), 7.37 (d, J=8.9 Hz, 2H), 7.36 (s, 1H), 3.35 (m, 8H), 3.26 (t, J=4.4 Hz, 4H), 2.79 (q, J=7.5 Hz, 2H), 1.23 (t, J=7.5 Hz, 3H). MS (ES+, m/z): 658.0 (M$^+$+1, 100.0).

Example 33

4-Piperazine-5-(4-trifluoromethyl-3-chlorobenzene)-N-benzenesulfonyl-7H-pyrrolo[2,3-d]pyrimidine $^1$H-NMR (CD$_3$OD/400 MHz): 8.36 (s, 1H), 7.83 (s, 1H), 7.79 (d, J=8.2 Hz, 1H), 7.65 (d, J=8.2 Hz, 1H), 7.52 (s, 1H), 3.26 (t, J=5.1 Hz, 4H), 2.70 (t, J=5.1 Hz, 4H). MS (ES+, m/z): 382.0 (M$^+$+1, 100.0).

Example 15

N-(4-(N-(5-ethyl-1,3,4-thiadiazo-2-yl)sulfamoyl)phenyl)-5-(4-trifluoromethyl-3-chlorophenyl)-7H-pyrrolo[2,3-d]pyrimidin-4-yl)piperazine-1-carbothioamide $^1$H-NMR (CD$_3$OD/CDCl$_3$/400 MHz): 8.41 (s, 1H), 7.86 (d, J=7.8 Hz, 1H), 7.86 (s, 1H), 7.75 (d, J=8.5 Hz, 2H), 7.70 (d, J=7.9 Hz, 1H), 7.58 (s, 1H), 7.41 (d, J=8.5 Hz, 2H), 3.88 (t, J=4.5 Hz, 4H), 3.42 (t, J=4.5 Hz, 4H), 2.82 (q, J=7.5 Hz, 2H), 1.29 (t, J=7.5 Hz, 3H). MS (ES+, m/z): 708.0 (M$^+$+1, 45.0).

Scheme 2
General Synthesis of Pyrrolo[2,3-d]pyrimidine Compoundsz

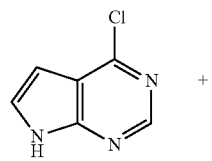

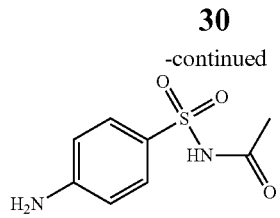

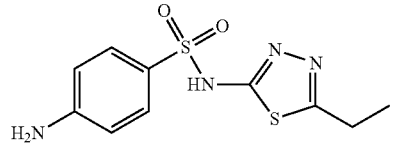

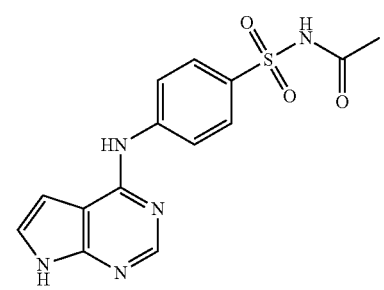

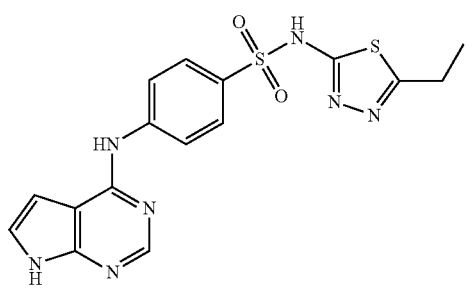

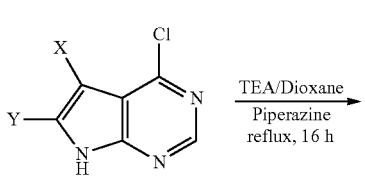

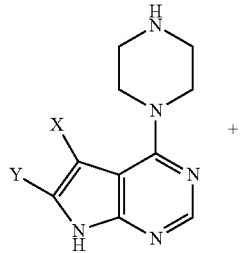

-continued

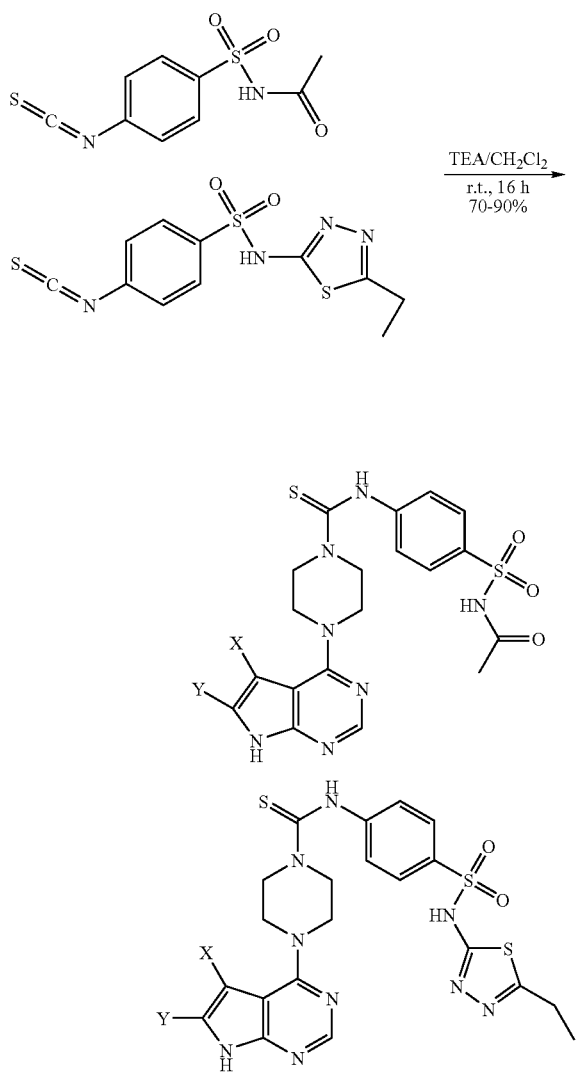

X, Y = H, F, Cl, CH₃, OCH₃, CF₃, OCF₃, CH=CHCl(F), CH₂CH₂F, CH₂CH₂CF₃, N(C₂H₄)₂NCH₃.

Example 4

N-(4-(7H-pyrrolo[2,3-d]pyrimidine-4-ylamino)phenylsulfonyl)acetamide $^1$H-NMR (DMSO-$d_6$/400 MHz): 11.92 (br, 2H), 9.77 (s, 1H), 8.36 (s, 1H), 8.15 (d, J=8.9 Hz, 2H), 7.85 (d, J=8.9 Hz, 2H), 7.31 (d, J=3.4 Hz, 1H), 6.84 (d, J=3.4 Hz, 1H), 1.90 (s, 3H). MS (ES+, m/z): 583.1 (M$^+$+1, 100.0).

Intermediate 4-(piperazin-1-yl)-7H-pyrrolo[2,3-d]pyrimidine $^1$H-NMR (CDCl₃/400 MHz): 8.13 (s, 1H), 7.12 (d, J=3.4 Hz, 1H), 6.60 (d, J=3.8 Hz, 1H), 3.91 (t, J=5.1 Hz, 4H), 2.94 (t, J=5.1 Hz, 4H). MS (ES+, m/z): 204.1 (M$^+$+1, 100.0).

Example 5

N-(4-(4-(7H-pyrrolo[2,3-d]pyrimidin-4-yl)piperazine-1-carbothioamido)phenylsulfonyl)acetamide $^1$H-NMR (DMSO-$d_6$/400 MHz): 8.16 (s, 1H), 7.81 (dd, J=6.8, 2.5 Hz, 2H), 7.60 (dd, J=6.8, 2.5 Hz, 2H), 7.20 (d, J=3.4 Hz, 1H), 6.65 (d, J=3.4 Hz, 1H), 4.06 (m, 8H), 1.92 (s, 3H). MS (ES+, m/z): 460.1 (M$^+$+, 100.0).

Example 6

4-(7H-pyrrolo[2,3-d]pyrimidin-4-ylamino)-N-(5-ethyl-1,3,4-thiadiazol-2-yl)benzenesulfonamide $^1$H-NMR (CD₃OD/400 MHz): 8.31 (s, 1H), 8.00 (d, J=8.9 Hz, 1H), 7.82 (d, J=8.9 Hz, 2H), 7.21 (d, J=3.4 Hz, 1H), 6.77 (d, J=3.4 Hz, 1H), 2.83 (q, J=7.5 Hz, 2H), 1.29 (t, J=7.5 Hz, 3H). MS (ES+, m/z): 402.1 (M$^+$+, 100.0).

Example 7

N-(4-(4-(5-(4-methoxyphenyl)thieno[2,3-d]pyrimidin-4-yl)piperazine-1-carbothioamido)phenylsulfonyl)acetamide $^1$H-NMR (CD₃OD/400 MHz): 8.16 (s, 1H), 7.79 (d, J=8.9 Hz, 2H), 7.52 (d, J=8.9 Hz, 2H), 7.15 (d, J=3.4 Hz, 1H), 6.68 (d, J=3.4 Hz, 1H), 4.16 (m, 8H), 2.84 (q, J=7.5 Hz, 2H), 1.29 (t, J=7.5 Hz, 3H). MS (ES+, m/z): 530.0 (M$^+$+, 100.0).

Intermediate 4,5-dichloro-7H-pyrrolo[2,3-d]pyrimidine $^1$H-NMR (DMSO-$d_6$/400 MHz): 12.57 (br, 1H), 8.58 (s, 1H), 7.92 (s, 1H). MS (ES+, m/z): 188.0 (M$^+$+, 100.0).

Intermediate 4-piperazine-5-chloro-7H-pyrrolo[2,3-d]pyrimidine $^1$H-NMR (CD₃OD/400 MHz): 8.23 (s, 1H), 7.26 (s, 1H), 3.92 (t, J=4.5 Hz, 4H), 3.65 (t, J=4.5 Hz, 4H). MS (ES+, m/z): 238.1 (M$^+$+, 100.0).

Example 16

N-(4-(N-(5-ethyl-1,3,4-thiadiazo-2-yl)sulfamoyl)phenyl)-5-(4-trifluoromethyl-3-chlorophenyl)-7H-pyrrolo[2,3-d]pyrimidin-4-yl)piperazine-1-carbothioamide $^1$H-NMR (CD₃OD/CDCl₃/400 MHz): 8.25 (s, 1H), 7.79 (d, J=8.9 Hz, 2H), 7.47 (d, J=8.9 Hz, 2H), 7.18 (s, 1H), 4.15 (t, J=4.5 Hz, 4H), 3.81 (t, J=4.5 Hz, 4H), 2.80 (q, J=7.5 Hz, 2H), 1.29 (t, J=7.5 Hz, 3H). MS (ES+, m/z): 564.0 (M$^+$+, 70.0).

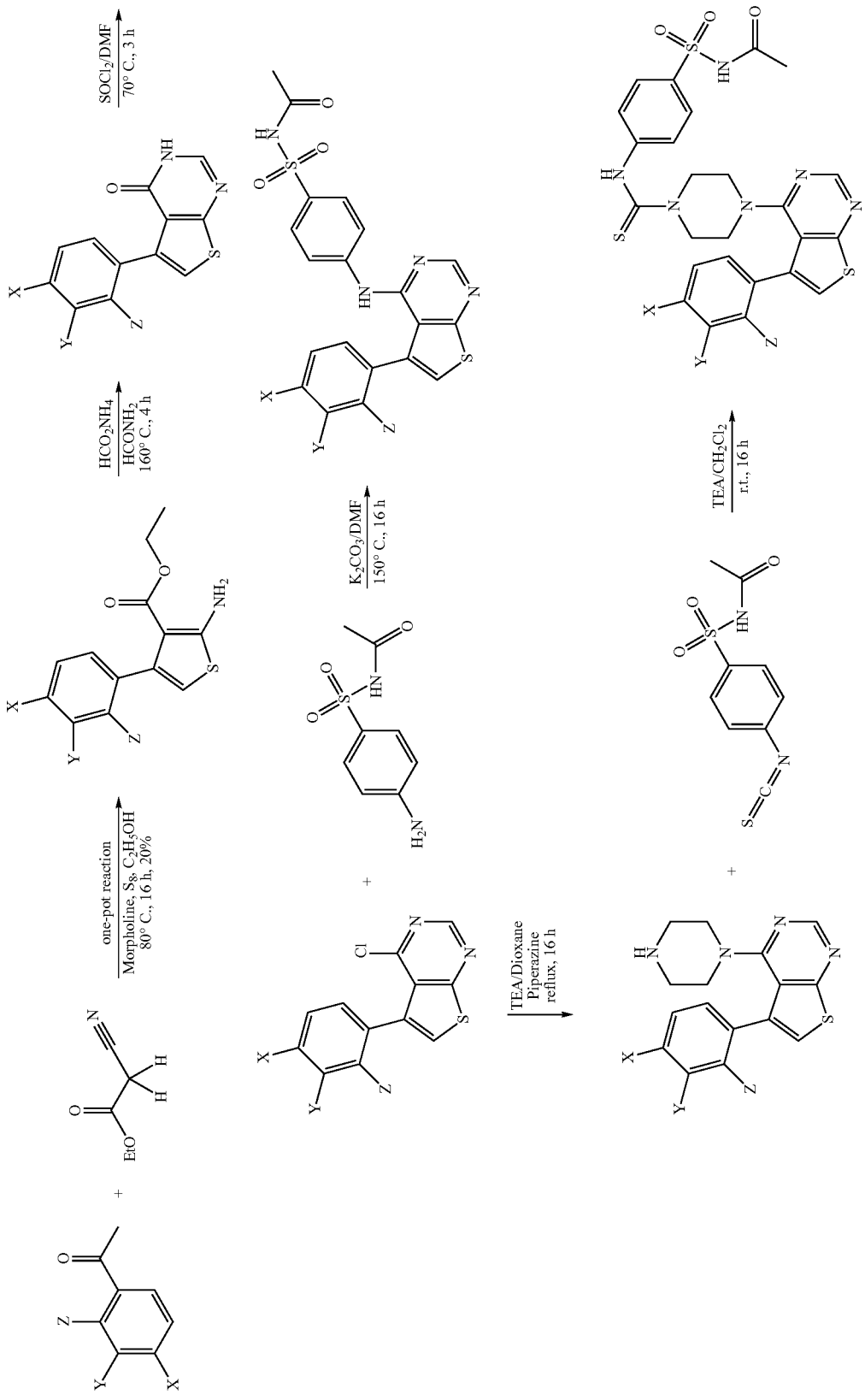

Intermediate 5-(Methoxyphenyl)thieno[2,3-d]pyrimidine-3H-4-one $^1$H-NMR (DMSO-d$_6$/400 MHz): 12.43 (s, 1H), 8.11 (d, J=4.7 Hz, 1H), 7.96 (dd, J=13.7, 1.4 Hz, 1H), 7.44 (s, 1H), 6.93 (dd, J=13.7, 2.0 Hz, 1H), 3.78 (s, 3H). MS (ES+, m/z): 258.90 (M$^+$+1, 100.0).

Intermediate

4-Chloro-5-(4-methoxyphenyl)thieno[2,3-d]pyrimidine $^1$H-NMR (DMSO-d$_6$/400 MHz): 8.85 (s, 1H), 7.41 (s, 1H), 7.32 (dd, J=13.7, 1.4 Hz, 1H), 6.95 (dd, J=13.7, 2.0 Hz, 1H), 3.86 (s, 3H). MS (ES+, m/z): 277.0 (M$^+$+1, 100.0).

Example 1

N-(4-(5-(4-methoxyphenyl)thieno[2,3-d]pyrimidine-4-ylamino)phenylsulfonyl)acetamide $^1$H-NMR (CDCl$_3$/CD$_3$OD/400 MHz): 8.63 (s, 1H), 7.88 (d, J=6.8 Hz, 2H), 7.51 (d, J=8.9 Hz, 2H), 7.42 (d, J=8.5 Hz, 2H), 7.34 (s, 1H), 7.09 (d, J=8.9 Hz, 2H), 3.90 (s, 3H), 1.91 (s, 3H). MS (ES+, m/z): 455.1 (M$^+$+1, 100.0).

Intermediate 5-(4-Methoxyphenyl)-4-(piperazin-1-yl)thieno[2,3-d]pyrimidine $^1$H-NMR (CDCl$_3$/CD$_3$OD/400 MHz): 8.57 (s, 1H), 7.41 (d, J=7.2 Hz, 2H), 7.40 (s, 1H), 7.03 (d, J=7.2 Hz, 2H), 4.77 (m, 4H), 3.85 (s, 3H), 3.38 (m, 4H). MS (ES+, m/z): 327.1 (M$^+$+1, 100.0).

Example 2

N-(4-(4-(5-(4-methoxyphenyl)thieno[2,3-d]pyrimidin-4-yl)piperazine-1-carbothioamido)phenylsulfonyl)acetamide $^1$H-NMR (CDCl$_3$/400 MHz): 8.56 (s, 1H), 8.46 (s, 1H), 7.81 (d, J=8.6 Hz, 2H), 7.34 (m, 4H), 7.18 (s, 1H), 6.94 (d, J=8.9 Hz, 2H), 3.84 (s, 3H), 3.65 (m, 4H), 3.30 (m, 4H), 2.04 (s, 3H). MS (ES+, m/z): 583.1 (M$^+$+1, 100.0).

Example 3

N-(4-(N-(5-ethyl-1,3,4-thiadiazol-2-yl)sulfamoyl)phenyl)-4-(5-(4-methoxyphenyl)thieno[2,3-d]pyrimidin-4-yl)piperazine-1-carbothioamide $^1$H-NMR (CD$_3$OD/400 MHz): 8.52 (s, 1H), 7.74 (d, J=8.9 Hz, 2H), 7.64 (s, 1H), 7.38 (m, 4H), 7.00 (d, J=8.6 Hz, 2H), 3.85 (s, 3H), 3.34 (m, 8H), 2.81 (q, J=7.5 Hz, 2H), 1.29 (t, J=7.5 Hz, 3H). MS (ES+, m/z): 653.1 (M$^+$+1, 100.0).

Scheme 4
Synthesis of 5-Pyrrolidine-pyrrolo[2,3-d]pyrimidine compounds

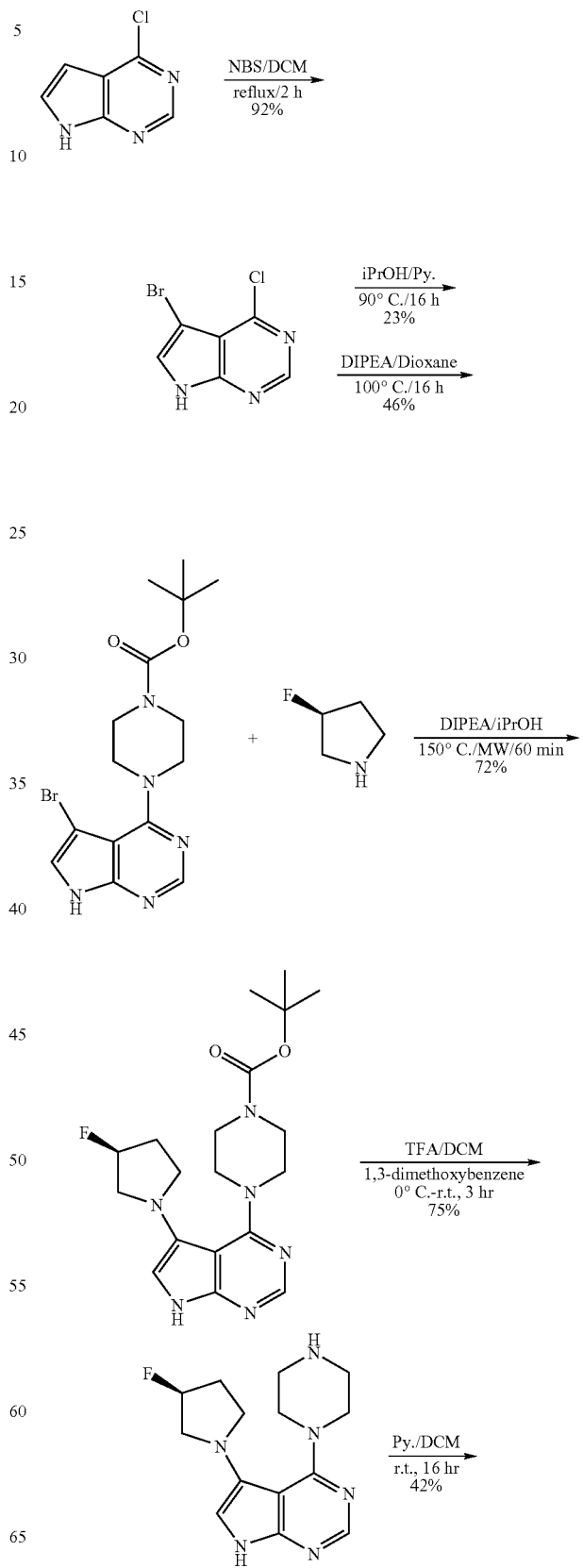

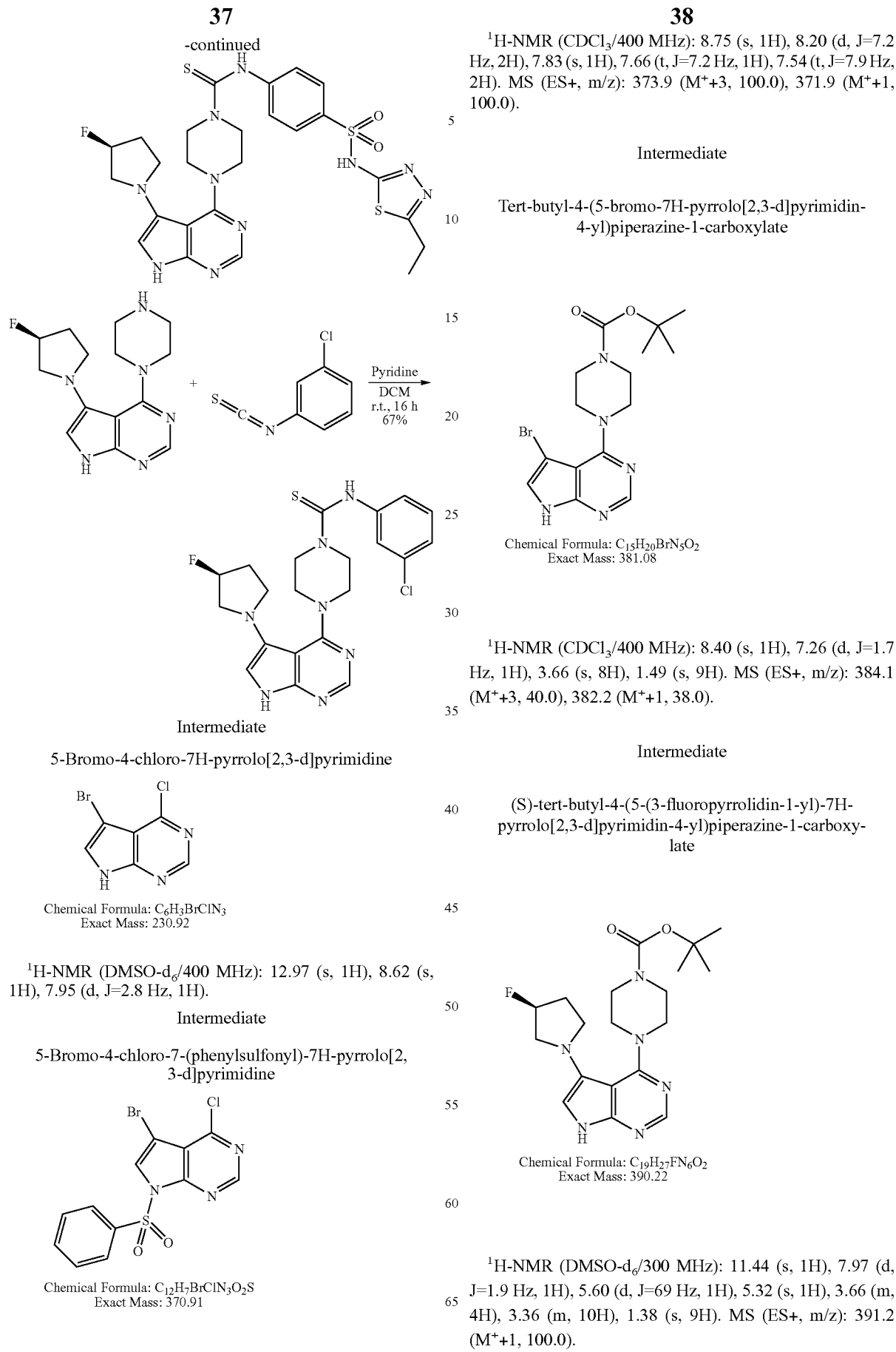
¹H-NMR (CDCl₃/400 MHz): 8.75 (s, 1H), 8.20 (d, J=7.2 Hz, 2H), 7.83 (s, 1H), 7.66 (t, J=7.2 Hz, 1H), 7.54 (t, J=7.9 Hz, 2H). MS (ES+, m/z): 373.9 (M⁺+3, 100.0), 371.9 (M⁺+1, 100.0).
Intermediate
Tert-butyl-4-(5-bromo-7H-pyrrolo[2,3-d]pyrimidin-4-yl)piperazine-1-carboxylate
¹H-NMR (CDCl₃/400 MHz): 8.40 (s, 1H), 7.26 (d, J=1.7 Hz, 1H), 3.66 (s, 8H), 1.49 (s, 9H). MS (ES+, m/z): 384.1 (M⁺+3, 40.0), 382.2 (M⁺+1, 38.0).
Intermediate
(S)-tert-butyl-4-(5-(3-fluoropyrrolidin-1-yl)-7H-pyrrolo[2,3-d]pyrimidin-4-yl)piperazine-1-carboxylate
¹H-NMR (DMSO-d₆/300 MHz): 11.44 (s, 1H), 7.97 (d, J=1.9 Hz, 1H), 5.60 (d, J=69 Hz, 1H), 5.32 (s, 1H), 3.66 (m, 4H), 3.36 (m, 10H), 1.38 (s, 9H). MS (ES+, m/z): 391.2 (M⁺+1, 100.0).

Intermediate (S)-5-(3-fluoropyrrolidin-1-yl)-4-(piperazin-1-yl)-7H-pyrrolo[2,3-d]pyrimidine

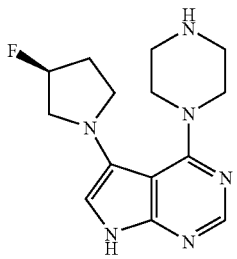

Chemical Formula: $C_{14}H_{19}FN_6$
Exact Mass: 290.17

$^1$H-NMR (CD$_3$OD/300 MHz): 8.38 (s, 1H), 7.12 (d, J=2.5 Hz, 1H), 6.46 (s, 1H), 5.45 (d, J=69 Hz, 1H), 4.11 (m, 4H), 3.75 (m, 6H), 3.38 (m, 4H). MS (ES+, m/z): 291.3 (M$^+$+1, 100.0).

Example 34

(S)—N-(4-(N-(5-ethyl-1,3,4-thiadiazol-2-yl)sulfamoyl)phenyl)-4-(5-(3fluoropyrrolidin-1-yl)-7H-pyrrolo[2,3-d]pyrimidin-4-yl)piperazine-1-carbothioamide

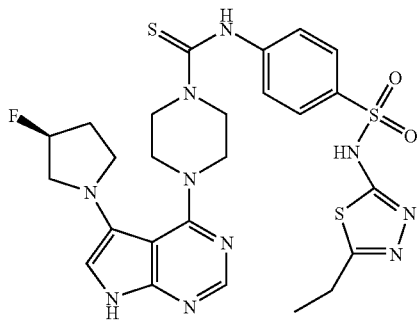

Chemical Formula: $C_{25}H_{29}FN_{10}O_2S_3$
Exact Mass: 616.16

$^1$H-NMR (CD$_3$OD/300 MHz): 8.23 (s, 1H), 7.77 (d, J=2.5 Hz, 2H), 7.44 (d, J=2.5 Hz, 2H), 5.39 (d, J=69 Hz, 1H), 4.08 (m, 4H), 3.89 (m, 6H), 3.75 (m, 4H), 3.16 (q, J=7.2 Hz, 4H), 1.29 (t, J=7.2 Hz, 1H). MS (ES+, m/z): 617.2 (M$^+$+1, 100.0).

Activity of Representative Axl Kinase Inhibitors

Axl lead compounds were tested for their ability to inhibit Axl enzyme activity in a biochemical assay. Briefly, in this assay kinase activity is determined by quantifying the amount of ATP remaining in solution following the kinase reaction by measuring the relative light units (RLU) produced by luciferase using a luminometer. Percent activity was determined for individual compounds by comparing luminometer readings of drug-treated reactions to controls containing no drug (RLU$_{No\ Inhib}$) and no Axl enzyme (RLU$_{No\ Kinase}$) in the following equation:

$$\text{Percent Inhibition} = \frac{RLU_{No\ Kinase} - RLU_{drug}}{RLU_{No\ Kinase} - RLU_{No\ Inhib}} \times 100$$

In a 50 µL reaction, 200 ng of recombinant Axl kinase (BPS Biosciences, San Diego, Calif.) was incubated at 30° C. for 2 h with shaking (360 rpm) with 10µγ Poly(Glu-Tyr) (Millipore Corp, Billerica, Mass.), 3 µM ATP (Invitrogen, Carlsbad, Calif.) and kinase reaction buffer (8 mM MOPS pH 7.0, 0.02 mM EDTA, 15 mM Magnesium chloride). The value of 3 µM ATP was determined to be the optimal concentration that gave maximum activity for the amount of enzyme used in this assay. This reaction was carried out in the presence of compounds which had been previously diluted to desired concentrations in DMSO. After incubation, 50 µL of Kinase-Glo® (Promega, Inc., Madison, Wis.) solution was added to each reaction mixture and allowed to equilibrate for 10 minutes at room temperature. Kinase-Glo solution contains luciferase enzyme and luciferin, which react with ATP to produce light. Kinase activity was determined by quantifying the amount of ATP remaining in solution following the kinase reaction by measuring the relative light units (RLU) produced by luciferase using a luminometer (Thermo Electron Corporation, Vantaa, Finland). IC$_{50}$ values were determined as the concentration of inhibitor required to reduce enzyme activity (ATP hydrolysis) to 50% of untreated levels. The IC$_{50}$ results obtained in these assays for representative Examples were between about 100 to 2.2 µM. It is advantageous that the IC$_{50}$ results be less than 50 µM. It is more advantageous that the IC$_{50}$ results be less than 10 µM.

Axl TR-FRET Assay (Lantha Screen/Lance Ultra)

Time-resolved fluorescence resonance energy transfer (TR-FRET) HTS assays are homogeneous proximity assays where the interaction of two dye-labeled binding partners is detected by the energy transfer between a donor and an acceptor dye, and the subsequent light emission by the acceptor dye. Currently, three LANCE TR-FRET platforms are available. They differ principally by the nature of the acceptor dye used for the energy transfer and by the substrate, which can be either directly labeled or biotinylated.

We used a TR-FRET platform that used a terbium chelate as a donor and fluorescein as an acceptor dye. This is the Lantha Screen platform developed by Invitrogen. Another platform includes a series of europium (Eu) chelate-labeled anti-phospho-substrate antibodies and several kinase substrates labeled with the ULight acceptor dye. The ULight dye is a small molecular weight fluorescent dye with a red-shifted emission. This platform has been developed by Perkin Elmer and may be used as well.

Time Resolved-Fluorescence Resonance Energy Transfer (TR-FRET) is emerging as one of the preferred fluorescent assay formats in drug discovery laboratories. TR-FRET assays are less susceptible to compound interference than other assay formats and may be applied to multiple target classes.

Procedure

This procedure describes how a LanthaScreen™ kinase assay is designed to detect and characterize Axl kinase inhibitors. The development is performed in three steps:

1. Optimization of Kinase Concentration Required to Determine ATP Km,app.

The assay is first performed at a high concentration of ATP (1 mM) against a dilution series of kinase in order to determine the amount of kinase required to elicit an approximately 80% change between the minimum and maximum TR-FRET emission ratios (the EC80 value).

2. Determination of ATP Km,app.

Using the concentration of enzyme determined in step 1, the assay is then performed against a dilution series of ATP in order to determine the amount of ATP required to elicit a 50% change between the minimum and maximum TR-FRET emission ratios (the EC50 value). This concentration of ATP is referred to as the "apparent" Km value for ATP, or the ATP Km,app.

3. Optimization of Kinase Concentration Required for Assay at ATP Km,app.

Using the ATP Km,app concentration of ATP determined in step 2, the kinase titration is repeated in order to determine the concentration of kinase required to elicit an approximately 80% change between the minimum and maximum TR-FRET emission ratios at the ATP Km,app concentration of ATP (the EC80 value). This is the concentration of kinase that will be used in an assay to determine an IC50 value for an inhibitor.

Using the ATP and kinase concentrations determined above, the reaction is then performed in the presence of a dilution series of inhibitor, and the amount of inhibitor required to elicit a 50% change in TR-FRET ratio (the IC50) is determined.

Reagents

All Obtained from Invitrogen Corporation
(www.invitrogen.com)

Kinase AXL PV3971 (10 µg)

Recombinant Human protein, Catalytic Domain (amino acids 473-894), Histidine-tagged, expressed in insect cells 99 nmole of phosphate transferred to Abl1 peptide substrate (EAIYAAPFAKKK) per minute per mg of total protein at 30° C. Activity determined at a final protein concentration of 8.33 µg/mL.

Kinase Reaction Buffer: 5× Kinase Buffer PV3189 (4 mL of 5×)

The kinase reaction buffer is supplied as a 5× concentrated stock. Prepare a 1× solution from this stock. The 1× kinase reaction buffer is stable at room temperature 1× kinase reaction buffer consists of 50 mM HEPES pH 7.5, 0.01% BRIJ-35, 10 mM MgCl2, and 1 mM EGTA Antibody LanthaScreen™ Tb-PY20 PV3552 (25 µg) PV3553 (1 mg)

The PY20 antibody is supplied at approximately 1 mg/mL. The molecular weight of the antibody is 150 kD. Thus, the stock concentration of the antibody is 6.7 µM, or 6700 nM.

Substrate Fluorescein-Poly GT PV3610 (1 mg)

The substrate is supplied at a concentration of 30 µM.

Antibody Dilution Buffer TR-FRET Dilution Buffer PV3574 (100 mL)

The antibody dilution buffer does not contain EDTA. EDTA is added separately, prior to addition of antibody.

500 mM EDTA Kinase Quench Buffer P2832 (10 mL)

10 mM ATP PV3227 (500 µL)

Comsumables 384-well low volume Proxiplate 384 Plus from Perkin Elmer Pipette tips, microcentrifuge tubes, etc.

Instruments

EnVision™ Xcite Multilabel Reader (PerkinElmer)

Four EXAMPLE compounds displayed results with the above assay of $IC_{50}$ from about 4.1 µM to less than about 0.3 µM. It is advantageous that the $IC_{50}$ results be less than 5.0 µM. It is more advantageous that the $IC_{50}$ results be less than 1.0 µM.

Any U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A compound according to Formula (I):

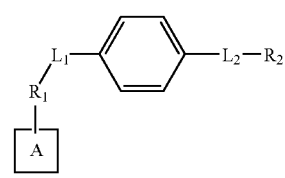

(I)

including stereoisomers, and pharmaceutically acceptable salts thereof, wherein:

ring moiety A is

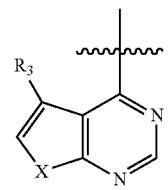

and wherein:

$L_1$ is —NH—, —C(=S)NH—, —C(=S)NHS(=O)$_2$—, or —C(=O)NH—;

$R_1$ is optional and if present is piperazinyl;

$L_2$=—S(=O)$_2$NH—, —S(=O)$_2$— or —NH—;

$R_2$ is heterocycle, substituted heterocycle, or —C(=O)R where R is alkyl;

X is NH; and $R_3$ is —H, halo, haloalkyl, haloalkoxy, aryl or substituted aryl.

2. The compound according to claim 1, wherein $L_1$ is —NH—.

3. The compound according to claim 1, wherein $L_1$ is —C(=S)NH—.

4. The compound according to claim 1, wherein $L_1$ is —C(=S)NHS(=O)$_2$—.

5. The compound according to claim 1, wherein $L_1$ is —C(=O)NH—.

6. The compound according to claim 1, consisting of:
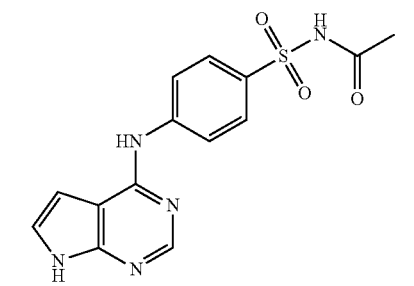
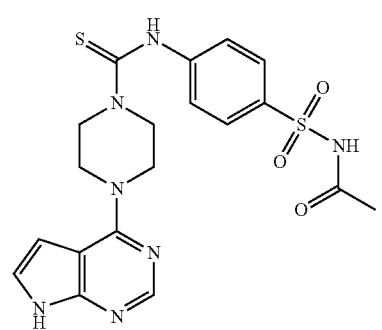
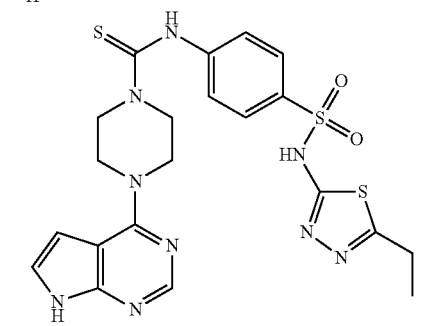
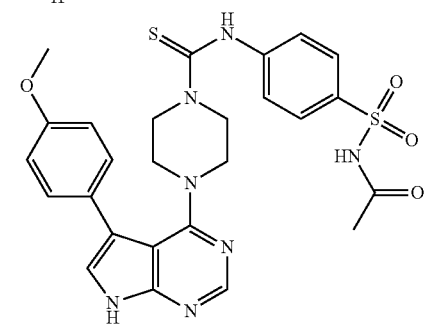
-continued
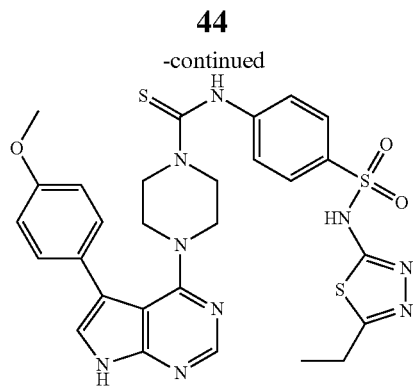
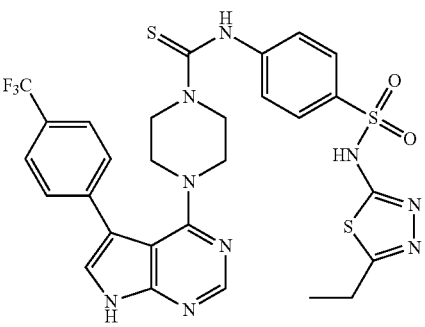
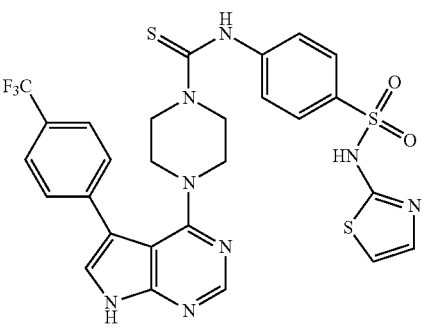
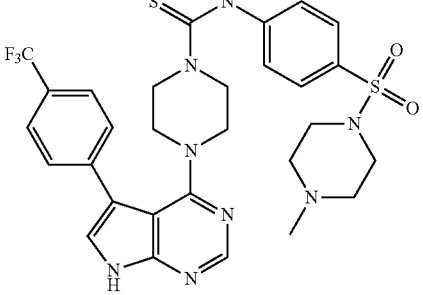
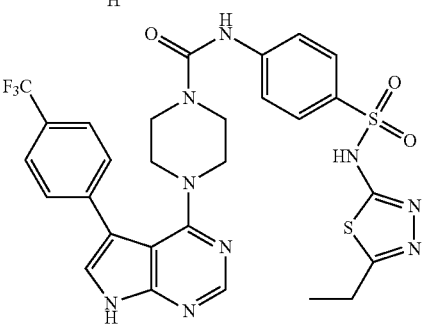

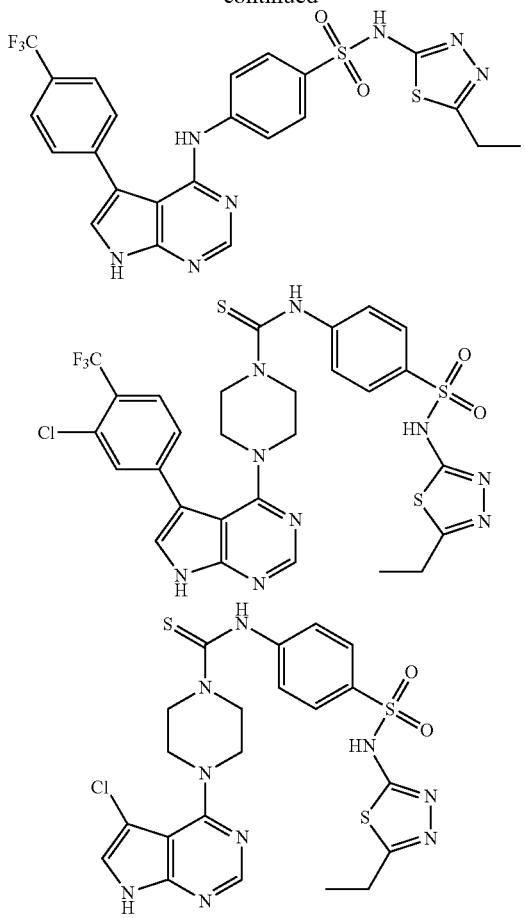

or a stereoisomer or pharmaceutically acceptable salt thereof.

7. The compound according to claim 1, consisting of:
4-Chloro-5-iodo-7-benzenesulfonyl-7H-pyrrolo[2,3-d]pyrimidine
7-Benzenesulfonyl-4-chloro-5-(4-methoxyphenyl)-7H-pyrrolo[2,3-d]pyrimidine
4-Piperazine-5-(4-methoxylbenzene)-7H-pyrrolo[2,3-d]pyrimidine
N-(4-(4-(4-methoxyphenyl)-7H-pyrrolo[2,3-d]piperazine-1-carbothioamido)phenylsulfonyl)acetamide
N-(4-(N-(5-ethyl-1,3,4-thiadiazol-2-yl)sulfamoyl)phenyl)-4-(5-(4-methoxyphenyl)-(7H-pyrrolo[2,3-d]pyrimidin-4-yl)piperazine-1-carbothioamide
N-(4-(N-(5-ethyl-1,3,4-thiadiazo-2-yl)sulfamoyl)phenyl)-5-(4-trifluoromethylphenyl)-7H-pyrrolo[2,3-d]pyrimidin-4-yl)piperazine-1-carbothioamide
N-(4-(N-thiazol-2-ylsulfamoyl)phenyl)-4-(5-(4-(trifluromethyl)phenyl)-7H-pyrrolo[2,3-d]pyrimidin-4-yl)piperazine-1-carbothioamide
N-(4-(4-methylpiperazin-1-ylsulfonyl)phenyl)-4-(5-(4-(trifluoromethyl)phenyl)-7H-pyrrolo[2,3-d]pyrimidin-4-yl)piperazine-1-carbothioamide
N-(4-(N-(5-ethyl-1,2,4-thiadiazo-2-yl)sulfamoyl)phenyl)-5-(4-trifluoromethylphenyl)-7H-pyrrolo[2,3-d]pyrimidin-4-yl)piperazine-1-carboamide
N-(4-(N-(5-ethyl-1,3,4-thiadiazo-2-yl)sulfamoyl)phenyl)-5-(4-trifluoromethyl-3-chlorophenyl)-7H-pyrrolo[2,3-d]pyrimidin-4-yl)piperazine-1-carbothioamide
N-(4-(7H-pyrroylo[2,3-d]pyrimidine-4-ylamino)piperazine-1-acetamide
N-(4-(4-(7H-pyrrolo[2,3-d]pyrimidin-4-yl)piperazine-1-carbothioamido)phenylsulfonyl)acetamide, and
4-(7H-pyrrolo[2,3-d]pyrimidin-4-ylamino)-N-(5-ethyl-1,3,4-thiadiazol-2-yl)benzenesulfonamide
or a stereoisomer or pharmaceutically acceptable salt thereof.

8. A composition comprising a compound according to claim 1 and a pharmaceutically acceptable excipient.

* * * * *